United States Patent [19]

Khouri

[11] Patent Number: 5,530,090
[45] Date of Patent: Jun. 25, 1996

[54] REDUCTIVE METHOD FOR PREPARATION OF MACROCYCLIC OLIGOMER MIXTURES

[75] Inventor: Farid F. Khouri, Clifton Park, N.Y.

[73] Assignee: General Electric Company, Schenectady, N.Y.

[21] Appl. No.: 419,565

[22] Filed: Apr. 10, 1995

[51] Int. Cl.⁶ ..................................................... C08G 73/10
[52] U.S. Cl. .................. 528/322; 528/15; 528/19; 528/21; 528/315; 528/319; 528/321
[58] Field of Search ............................ 528/15, 19, 21, 528/315, 319, 322

[56] References Cited

U.S. PATENT DOCUMENTS 3,890,272   6/1975   D'Alelio .................................. 528/170
5,357,029  10/1994   Takekoshi et al. ..................... 528/322
5,399,715   3/1995   Naitoh et al. ........................... 548/521

FOREIGN PATENT DOCUMENTS 0317226   5/1989   European Pat. Off. .

OTHER PUBLICATIONS

Colquhoun et al., J. Chem. Soc., Chem Commun. The month of publication is not available. 1990, 336–339.

*Primary Examiner*—Samuel A. Acquah
*Assistant Examiner*—P. Hampton-Hightower
*Attorney, Agent, or Firm*—William H. Pittman

[57] ABSTRACT

Macrocyclic oligomer mixtures, particularly polyimide oligomer mixtures, are prepared by the treatment of a dihalo-substituted organic compound or the like under reducing conditions, preferably by a complex of a zerovalent Group VIII metal. Cyclization takes place by reductive dehalogenation.

12 Claims, No Drawings

REDUCTIVE METHOD FOR PREPARATION OF MACROCYCLIC OLIGOMER MIXTURES

BACKGROUND OF THE INVENTION

This invention relates to the preparation of macrocyclic oligomer compositions, and more particularly to a preparative method involving reductive dehalogenation or a process analogous thereto.

Macrocyclic polyimide oligomers are described in U.S. Pat. No. 5,357,029. The method for their preparation described therein involves the reaction of at least one diamine with at least one aromatic tetracarboxylic acid or dianhydride thereof under specified conditions, including high dilution. Other methods requiring high dilution have also been described. The macrocyclic oligomers thus obtained are capable of ring-opening polymerization to form high molecular weight linear polyimides.

The preparation of various types of macrocyclic oligomers, similarly capable of ring-opening polymerization, is described in European patent application 317,226. This method involves a reductive dehalogenation procedure employing a metal such as nickel, typically in the zerovalent state as the result of reduction by a more electropositive metal such as zinc and in the form of a complex with a triarylphosphine. It also requires high dilution, the procedure including a step of dropwise addition of a solution of a dihalo compound to a suspension of the catalyst. A typical solvent employed is dimethylacetamide. The products are described as pure macrocyclic oligomers containing one or two structural units, as shown by various analytical methods including their very high and relatively narrow melting point ranges.

From a commercial standpoint, it would be desirable to minimize the need for solvents in the production of macrocyclic oligomers capable of polymerization. It would also be desirable to obtain as a product a mixture of macrocyclic oligomers rather than a single oligomer, since such mixtures have much lower melting points than individual molecular species and may thus be handled and polymerized in liquid form at much lower temperatures.

Accordingly, the present invention provides a method for the preparation of macrocyclic oligomers which is not dependent on dissolution of the monomeric precursor in a solvent and which produces macrocyclic oligomers in the form of a relatively low melting mixture.

SUMMARY OF THE INVENTION

The invention is a method for preparing a cyclic oligomer mixture which comprises reductively cyclizing a disubstituted compound of the formula

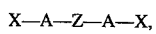

X—A—Z—A—X, wherein each X is independently chloride, bromide, iodide, carboxylate, sulfonate or $B(OR)_2$ wherein R is hydrogen, alkyl or aryl; A is a divalent organic radical containing at least one aromatic ring and Z is a divalent bridging group, by adding said disubstituted compound neat, under reducing conditions, to a reaction mass comprising an organic liquid which is substantially inert under said reducing conditions and in which said disubstituted compound fully dissolves, under the reaction conditions employed, only within at least ten minutes.

DETAILED DESCRIPTION; PREFERRED EMBODIMENTS

In the disubstituted compounds employed according to the invention, the two X groups per molecule may be different but are usually the same. Suitable carboxylic groups include acetate; sulfonate groups include methanesulfonate, p-toluenesulfonate and trifluoromethanesulfonate. The halogens and especially chlorine are preferred.

The A radical is any divalent radical containing at least one aromatic ring. Thus, monocyclic radicals such as p- and m-phenylene are included. Also included are fused and linked polycyclic radicals and especially phthalimido radicals in which the X value is at the 3- or 4-position, preferably the 4-position, of the aromatic ring.

The molecular structure of the bridging group, Z, is not critical but may encompass essentially any divalent radical or atom capable of forming covalent bonds. Suitable groups include oxygen, sulfur, NH, $SO_2$, m- and p-phenylene, biphenylene and combinations thereof. Unsymmetrical groups in which a 3-phenylene and 4-phenylene radical are linked by a bridging atom are frequently preferred. They include such structures as (3-phenylene)(4-phenylene)oxy, which is often preferred.

A particularly preferred disubstituted compound is the bisimide condensation product of 4-chlorophthalic anhydride and 3-aminophenyl 4-aminophenyl ether, also known as 3,4'-oxydianiline. Said condensation product produces macrocyclic polyetherimide oligomers convertible to linear polyimides with very high thermal resistance, particularly useful as high temperature adhesives.

According to the invention, the disubstituted compound is added neat (i.e., in the absence of solvents and diluents), under reducing conditions, to a reaction mass comprising an organic liquid which is substantially inert under the reducing conditions employed. The nature of the organic liquid is not otherwise critical except that it must be one in which said disubstituted compound fully dissolves, under the reaction conditions employed, only within at least 10 minutes and preferably at least 15 minutes. Under these conditions, the disubstituted compound is effectively present in reactive form only in high dilution.

Those skilled in the art will readily be able to determine what organic liquids are suitable for a specific reaction. When the preferred disubstituted compound described above (i.e., the bisimide condensation product of 4-chlorophthalic anhydride and 3,4'-oxydianiline) is employed, suitable liquids include dimethylformamide, dimethylacetamide, tetrahydrofuran and pyridine. Dimethylformamide (DMF) and dimethylacetamide are particularly suitable. At about 25° C., said condensation product is essentially completely insoluble in these solvents; at 50° C., its solubility is about 250 mg/100 ml; and at 70° C., a typical reaction temperature, its solubility is at least 540 mg/100 ml but only after stirring for 15 minutes.

The reducing conditions employed in the method of this invention may vary widely in nature. Thus, electrochemical or chemical reduction may be employed, with chemical reduction being preferred under most circumstances.

Chemical reduction is typically effected by a catalyst formed by the reaction of a metal-containing compound with a reducing agent which, under the conditions of the reaction, converts said metal-containing compound to a complex of a zerovalent metal, particularly a Group VIII metal; that is, iron, cobalt, nickel, ruthenium, rhodium, palladium, osmium, iridium or platinum. Such catalysts may, for example, be prepared by the action of a complexing agent such as a triarylphosphine, preferably triphenylphosphine, and a reducing agent such as elemental zinc, magnesium or mercury, sodium borohydride, lithium aluminum hydride or trialkylaluminum reagents, on a salt of the transition metal, such as nickel chloride or ferric chloride.

The combination of nickel chloride, triphenylphosphine and metallic zinc is particularly preferred, especially in the presence of catalyst promoters, typically alkali metal halides such as sodium bromide, and modifiers such as dipyridyl which suppress premature reductive dehalogenation or the like. The preparation of such a combination is described in Colon et al., *J. Orgo Chem.*, 51, 2627 (1986), and Ueda et al., *J. Poly. Sci., Part A*, 32, 675–681 (1994). For example, a combination of triphenylphosphine and nickel chloride in a molar proportion of about 3–5:1 and metallic zinc, ordinarily in the form of activated zinc dust, in a molar ratio to nickel of about 15–25:1, may be suspended in the organic liquid. Also present, preferably, are sodium bromide and 2,2'-dipyridyl in molar ratios to nickel in the ranges of about 5–8:1 and 0.8–1.2:1.

The disubstituted organic compound is added neat (i.e., without solvents or additional chemicals) to the reducing mixture, ordinarily at a temperature in the range of about 60°–90° C. Addition is preferably gradual, typically portionwise, although it is within the scope of the invention to add said compound in a single batch. Heating at this temperature may then be continued until reduction is complete. The macrocyclic oligomer mixture formed may be isolated by conventional means such as vacuum stripping or precipitation with a non-solvent. It may contain, in addition to the macrocyclic oligomers, substantial proportions of linear oligomers.

The macrocyclic oligomer compositions prepared by the method of this invention may be polymerized to linear polymers by conventional means. These include, in the case of macrocyclic polyimide oligomers, the method disclosed in the aforementioned U.S. Pat. No. 5,357,029. Macrocyclic oligomers of other types may be polymerized as disclosed in the aforementioned European patent application 317,226. Said patent and application are incorporated by reference herein.

The method of this invention is illustrated by the following examples.

EXAMPLE 1

A 250-ml 3-necked round-bottomed flask equipped with a mechanical stirrer and a Dean-Stark trap was charged with 120 ml of o-dichlorobenzene, 25 ml of toluene and 10.878 g (59.6 mmol) of 4-chlorophthalic anhydride. The mixture was stirred until the 4-chlorophthalic anhydride had dissolved. There was then added 5.849 g (29.21 mmol) of 3,4'-oxydianiline and the mixture was stirred at reflux under nitrogen for 30 minutes, whereupon it became clear and water started to collect in the trap. Refluxing was continued for 9 hours, after which the mixture was cooled to room temperature and a solid product precipitated. The solid was filtered, washed three times with toluene and acetone and dried at 160° C. under vacuum for 18 hours. The yield of the desired bisimide condensation product was 13 g (84% of theoretical).

EXAMPLE 2

A 50-ml 3-necked round-bottomed flask was dried in an oven and charged with 20 mg (0.154 mmol) of nickel chloride, 186 mg (0.709 mmol) of triphenylphosphine, 200 mg (3.05 mmol) of activated zinc dust, 97.3 mg (0.945 mmol) of sodium bromide and 24.1 mg (0.154 mmol) of 2,2'-dipyridyl. There was then added, via a syringe, 25 ml of dry DMF (distilled from calcium oxide). The mixture was stirred in a nitrogen atmosphere and heated at 70° C. until the catalyst mixture developed a reddish brown color. There was then added 1 g (1.89 mmol) of the product of Example 1, in 7 portions at 10-minute intervals. Heating and stirring were continued for 17 hours, after which the mixture was cooled, diluted with 100 ml of tetrahydrofuran, heated to 40° C. and again cooled. The resulting precipitated solid was removed by filtration, washed with tetrahydrofuran and dried. Analysis by high pressure liquid chromatography, gel permeation chromatography and field desorption mass spectroscopy showed the presence of macrocyclic oligomers having degrees of polymerization of 2–6.

What is claimed is:

1. A method for preparing a cyclic oligomer mixture which comprises reductively cyclizing a disubstituted compound of the formula

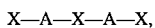

X—A—X—A—X, wherein each X is independently chloride, bromide, iodide, carboxylate, sulfonate or B(OR)$_2$ wherein R is hydrogen, alkyl or aryl; A is a divalent organic radical containing at least one aromatic ring and Z is a divalent bridging group, by gradually adding said disubstituted compound neat, under reducing conditions including temperatures in the range of about 60°–90° C. and the presence of a catalyst which is a complex of a zero valent Group VIII metal, to a reaction mass comprising an organic liquid which is substantially inert under said reducing conditions and in which said disubstituted compound fully dissolves, under the reaction conditions employed, only within at least ten minutes.

2. A method according to claim 1 wherein each X is chlorine, bromine or iodine.

3. A method according to claim 2 wherein A is a phthalimido radical in which the X value is at the 4-position.

4. A method according to claim 3 wherein Z is (3-phenylene) (4-phenylene)oxy.

5. A method according to claim 4 wherein each X is chlorine.

6. A method according to claim 1 wherein the zerovalent metal is nickel.

7. A method according to claim 6 wherein the catalyst is a triarylphosphine complex of zerovalent nickel.

8. A method according to claim 7 wherein the triarylphosphine is triphenylphosphine.

9. A method according to claim 1 wherein the organic liquid is dimethylformamide, dimethylacetamide, tetrahydrofuran or pyridine.

10. A method according to claim 9 wherein the organic liquid is dimethylformamide or dimethylacetamide.

11. A method according to claim 1 wherein said disubstituted compound is added in one portion.

12. A method according to claim 1 wherein said disubstituted compound is added gradually.

* * * * *